US00PP28177P2

(12) United States Plant Patent
Hansen

(10) Patent No.: US PP28,177 P2
(45) Date of Patent: Jul. 11, 2017

(54) ***BUDDLEIA* PLANT NAMED 'MAGENTA MUNCHKIN'**

(50) Latin Name: ***Buddleia* hybrid**
Varietal Denomination: Magenta Munchkin

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 14/999,592

(22) Filed: May 31, 2016

(51) Int. Cl.
*A01H 5/00* (2006.01)

(52) U.S. Cl.
USPC ..... Plt./242

(58) Field of Classification Search
USPC ..... Plt./242
See application file for complete search history.

*Primary Examiner* — Annette Para

(57) ABSTRACT

*Buddleia* 'Magenta Munchkin' is a short, compact, mounded, multi-stemmed, winter-hardy butterfly bush with long, dense-flowering, outward to slightly drooping thyrse with sweetly-fragrant fuchsia-red flower faces and yellowish orange throats starting early from mid-summer until frost, from soil line to top of plant, that are attractively offset by dark green foliage with silvery white undersides.

1 Drawing Sheet

Botanical classification: *Buddleia* hybrid.
Variety denomination: 'Magenta Munchkin'.

BACKGROUND OF THE PLANT

The present invention relates to the new and distinct butterfly bush plant, *Buddleia* 'Magenta Munchkin' hybridized by Hans A. Hansen in the summer of 2012 at a wholesale perennial nursery in Zeeland, Mich., USA. 'Magenta Munchkin' is the result of an ongoing breeding program conducted by the inventor. The goals for this program have been to produce improved, garden-worthy plants for the ornamental plant market. The new plant, originally assigned breeder code H12-109-01, is a single seedling selected from an open pollination of the proprietary unreleased hybrid named *Buddleia* H11-38-06 (not patented) as the female or seed parent. The male parent is unknown, but may have been from any one of several proprietary within the breeding field.

No plants of *Buddleia* 'Magenta Munchkin' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

*Buddleia* 'Magenta Munchkin' was first asexually propagated from a single select plant in 2013 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

The following traits have been repeatedly observed and are determined to be the unique characteristics of 'Magenta Munchkin'.

The nearest comparison plants are *Buddleia* 'Miss Ruby' U.S. Plant Pat. No. 19,950, *Buddleia* 'Miss Molly' U.S. Plant Pat. No. 23,425 and *Buddleia* 'Attraction' (not patented). All of the above have flowers with coloration in the reddish range. All of the above are much taller and less compact than 'Magenta Munchkin'. Compared to the new plant, 'Miss Ruby' has smaller inflorescences in width and length and individual flower faces are more reddish purple. Compared to 'Miss Molly' the new plant has much larger inflorescences and the flower faces are less in the red hue and closer to purple. The *Buddleia* with the nearest flower color is 'Attraction', but the plant habit as well as inflorescence size is much larger than the new plant.

*Buddleia* 'Magenta Munchkin' is a unique winter-hardy butterfly bush different from all other *Buddleia* cultivars known to the inventor based on the following combined traits:

1. Winter-hardy shrub, with multiple-stemmed, short, compact, round-mounded habit.
2. Many-flowered, dense, outward to slightly drooping thyrse starting early and over a prolonged season beginning mid-summer and continuing until frost, flowering from soil line to top of plant.
3. Individual flowers with flat faces of fuchsia-red and throats of yellowish orange.
4. Lanceolate foliage of dark green with silvery-white, canescent undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
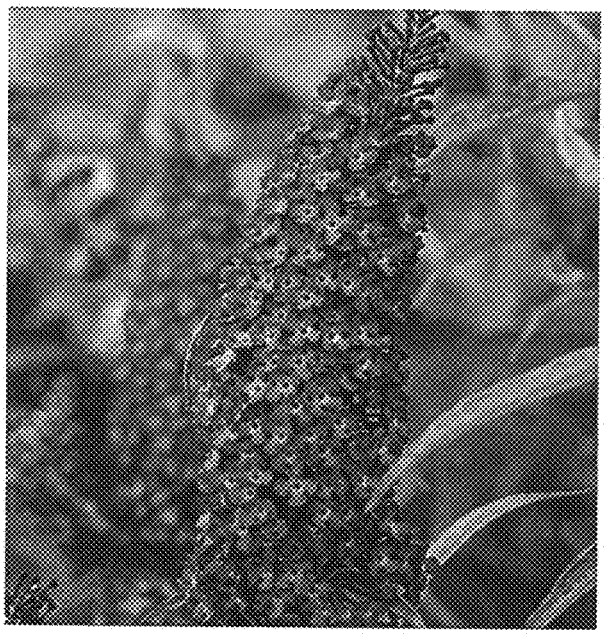
FIG. 1 shows a close-up of the flowers and buds.
Figure 2:
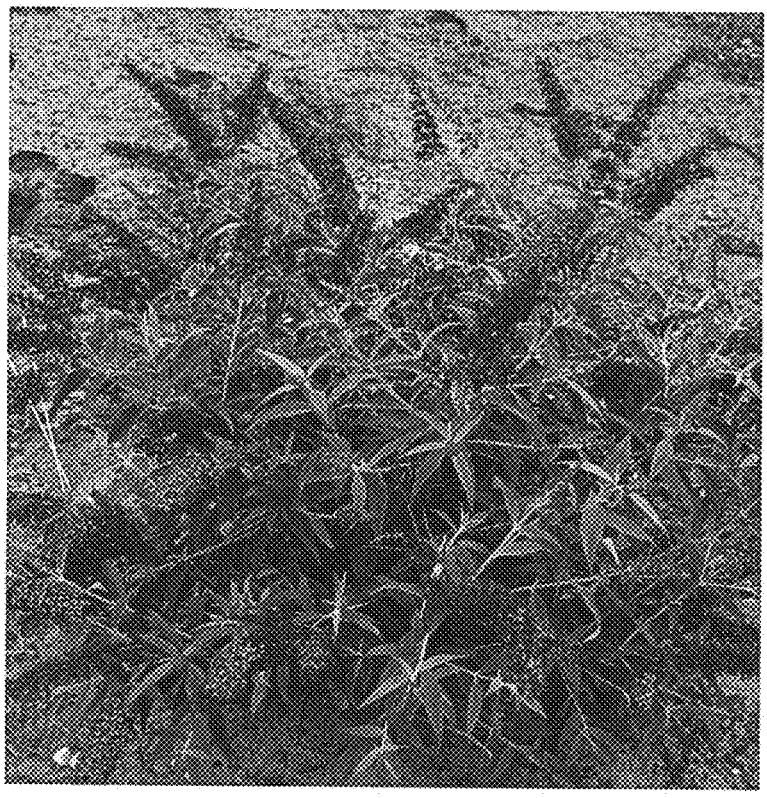
FIG. 2 shows the habit of a two-year-old plant in mid-season flowering.

The following descriptions and color references are based on the 2001 edition of The Royal Horticultural Society Colour Chart except where common dictionary terms are used. The new plant, *Buddleia* 'Magenta Munchkin', has not been observed under all possible conditions. The phenotype may vary slightly with different environmental conditions, such as temperature, light, fertility, moisture and maturity levels, but without any change in the genotype. The following observations and size descriptions are of two-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: Proprietary hybrid H11-38-06 (not patented) as the female or pod parent times an unknown open-pollination as the male or pollen parent.

Propagation:

*Method*.—Softwood cuttings.

*Time to initiate roots from tissue culture*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type.

*Crop time*.—Under normal spring growing conditions 6 to 7 weeks to fill and flower in a four-liter container a 65 mm liner; 8 to 10 weeks to finish and flower in a four-liter container from a 25 mm liner; Plant vigor is very good.

Plant description:

*Plant shape and habit*.—Winter-hardy, herbaceous, semi-woody, well-branched shrub with about 16.0 mm thick upright and branched main stems producing outward to slightly drooping thyrse in a compact rounded mound of about 90.0 cm tall and about 108.0 cm wide.

*Stem*.—Terete and woody in lower portion with exfoliating bark; younger upper portion puberulent and quadrangular in cross section with ridges in corners; strong and flexible; average about 85 cm tall from soil line to just below terminal flowers, and about 1.6 cm diameter at the base; before distal flowers about 12 secondary branches.

*Stem color*.—Distal portion just below flowers between RHS 138C and RHS 138B with tinting of between RHS 187B and RHS N186C where exposed to more intense light, and in about basal 10 cm between RHS 167C and RHS 165C with striations between RHS 200A and RHS N199B.

*Plant size*.—Unpinched plant with stems flowering to about 90 cm tall; overall plant about 108.0 cm wide.

*Internode*.—About 12 nodes per stem below flowers, average internode length about 7.0 cm on unpinched plant; upper internodes slightly more elongated than lower internodes.

Foliage description: Opposite, decussate; serrulate; canescent abaxial and puberulent adaxial; lanceolate with attenuate base and narrowly acute apex; no foliar fragrance detected; Leaf blade size: up to about 7.8 cm long and about 2.1 cm wide, average about 7.2 cm long and about 1.7 cm wide; becoming smaller in distal portion of stem.

*Foliage color*.—Young expanding leaf adaxial side blend between RHS 188C and RHS 194C, young expanding abaxial between RHS 194D and lighter than RHS 148D; mature leaves adaxial side between RHS 137A and RHS 137B, abaxial between RHS 194D and lighter than RHS 148D.

*Veins*.—Reticulate; abaxial costate, adaxial slightly impressed.

*Vein color*.—Young expanding adaxial center midrib and lateral veins nearest RHS 192D, abaxial young expanding veins nearest RHS 192D; mature adaxial midrib and lateral veins nearest RHS 138C, abaxial midrib and lateral veins nearest RHS 145D.

*Petioles*.—Glaucous and puberulent adaxial, pubescent abaxial; partially applanate adaxial; average size about 0.4 cm long and about 1.0 mm wide at the point of attachment to stem.

*Petiole color*.—Nearest RHS 192C adaxial and nearest RHS 145D abaxial.

*Inflorescence description*.—Glomerate thyrse consisting of about 500 self-cleaning salverform flowers; to about 18.0 cm long and about 6.5 cm across; beginning early in mid-July and continuing until frost in Michigan; attitude outward facing with distal portion slightly drooping.

*Buds*.—Elongated clavate with straight tube, apex rounded; one day prior to opening about 9.0 mm long and about 3.0 mm diameter in club and throat about 1.0 mm diameter in throat and about 6.0 mm long.

*Bud color*.—Nearest RHS 61A in club portion and tube portion nearest RHS 64A.

*Sepals*.—Typically four, proximal two-thirds connate, adpressed to corolla tube; narrowly acute apex; glabrous adaxial and pubescent abaxial; margin entire, edentate; fused in about the basal 2.2 mm and split in about the terminal 1.3 mm; forming a corolla about 3.5 mm long and about 1.5 mm across; individually less than about 1.0 mm wide at point of fusion.

*Sepal color*.—Adaxial nearest RHS 138C, abaxial between RHS 145A and RHS 139C.

*Flowers fragrance*.—Pleasantly and distinctly sweet.

*Flower attitude*.—Upward and outward.

*Lastingness of inflorescence*.—About 10 to 12 days.

*Lastingness of individual flower*.—About 3 to 5 days.

*Petals*.—Four; glabrous; petal blade rounded with crenate margin; petals fused into salverform with typically straight cylindrical tube about 10.0 mm long and 1.0 mm diameter, and a slightly cupped face about 7.0 mm across; blade to about 3.0 mm across and about 3.0 mm long from fused face; overall length about 12.0 mm and face about 7.0 mm across.

*Petal color*.—Adaxial center nearest RHS 155D in the 1.0 mm tube base merging to a 1.0 mm band of nearest RHS 14C and the distal 8.0 mm of tube between RHS 184B and RHS 70A and petal blades of nearest RHS N80A toward margin and nearest RHS N80B toward eye; abaxial face blades nearest RHS N80A toward margin and nearest RHS N80B toward eye, abaxial tube basal 1.0 mm nearest RHS 155D merging to 1.0 mm section of about 14C and middle portion nearest RHS N170A with section closest blades nearest RHS N25B.

*Gynoecium*.—Pistil: one; about 3.5 mm long. Style: short, round, glabrous; about 1.4 mm long and less than 0.2 mm diameter; color nearest RHS 144C. Stigma: oblong, minutely puberulent; about 0.2 mm in diameter and about 0.6 mm long; color nearest RHS 144B. Ovary: superior; globose; about 1.0 mm across at base and 1.5 mm tall; distally tapering to style; color between RHS 144A and RHS 144B.

*Androecium*.—Filaments: not produced or very short. Anthers: typically four; oblong; introrse; adnate to about mid-point of corolla tube; about 1.0 mm long and about 0.3 mm wide; color nearest RHS 11D. Pollen: globose, less than 0.1 mm long; color nearest RHS 14D.

*Pedicel*.—short, puberulent; about 1.0 mm long and about 0.2 mm diameter; color lighter than RHS N138D.

*Peduncle*.—Quadrangular, pubescent, flexible and strong; flowering portion to about 18.0 cm long.

*Peduncle color*.—Lighter than RHS N138D.

*Fruit*.—Not observed.

*Seed*.—Not observed.

Disease resistance: Resistance has been noted to deer browsing. Other resistance beyond that of known butterfly bush cultivars has not been observed. The plant grows best with plenty of moisture and adequate drainage, but is able to tolerate some drought when mature. Hardiness at least from USDA zone 6 through 10.

I claim:

1. A new cultivar of winter-hardy butterfly bush *Buddleia* plant named 'Magenta Munchkin' as herein illustrated and described, especially suitable for potted plant culture, landscaping as a specimen or en masse or as cut flower purposes.

* * * * *